United States Patent
Medoff

[19]

[11] Patent Number: 6,077,266
[45] Date of Patent: Jun. 20, 2000

[54] METHOD OF ENABLING BONE SCREWS TO BE INSTALLED AT AN ANGLE IN UNDERLYING BONE

[76] Inventor: Robert J. Medoff, 159 Ku'ukama St., Kailua, Hi. 96734

[21] Appl. No.: 09/234,138

[22] Filed: Jan. 19, 1999

[30] Foreign Application Priority Data

Jan. 15, 1999 [SE] Sweden ................................. 9900094

[51] Int. Cl.[7] .................................................. A61B 17/80
[52] U.S. Cl. ................................ 606/69; 606/60; 606/72; 128/898
[58] Field of Search ................................ 606/60, 61, 69, 606/70, 71, 72, 73; 128/898

[56] References Cited

U.S. PATENT DOCUMENTS

| | | | |
|---|---|---|---|
| 3,716,050 | 2/1973 | Johnston . | |
| 3,779,240 | 12/1973 | Kondo . | |
| 4,493,317 | 1/1985 | Klaue . | |
| 4,565,193 | 1/1986 | Streli . | |
| 4,651,724 | 3/1987 | Berentey et al. . | |
| 5,085,660 | 2/1992 | Lin | 606/73 |
| 5,197,966 | 3/1993 | Sommerkamp | 606/69 |
| 5,304,180 | 4/1994 | Slocum | 606/69 |
| 5,484,439 | 1/1996 | Olson et al. | 606/65 |
| 5,534,027 | 7/1996 | Hodorek | 623/16 |
| 5,558,674 | 9/1996 | Heggeness et al. | 606/61 |
| 5,578,036 | 11/1996 | Stone et al. | 606/69 |
| 5,586,985 | 12/1996 | Putnam et al. | 606/69 |
| 5,718,704 | 2/1998 | Medoff | 606/69 |

FOREIGN PATENT DOCUMENTS

| | | |
|---|---|---|
| 0382256 | 8/1990 | European Pat. Off. . |
| 2291734 | 6/1976 | France . |
| 2320078 | 3/1977 | France . |
| 2405062 | 5/1979 | France . |
| 2405705 | 5/1979 | France . |
| 2472373 | 7/1981 | France . |
| 2501033 | 9/1982 | France . |
| 1827209 | 7/1993 | U.S.S.R. . |
| 1300449 | 12/1972 | United Kingdom . |
| 2158716 | 11/1985 | United Kingdom . |

*Primary Examiner*—Michael Buiz
*Assistant Examiner*—David O. Reip
*Attorney, Agent, or Firm*—Ladas & Parry

[57] ABSTRACT

In order to install a fracture fixation fastener at an acute angle in an underlying bone in a hole is provided in a support plate at a particular angle and with a particular diameter in relation to the thickness of the plate and the diameter of the fastener to enable the fastener to be installed within a pre-determined angular range which is asymmetrical relative to a line perpendicular to the plate.

4 Claims, 2 Drawing Sheets

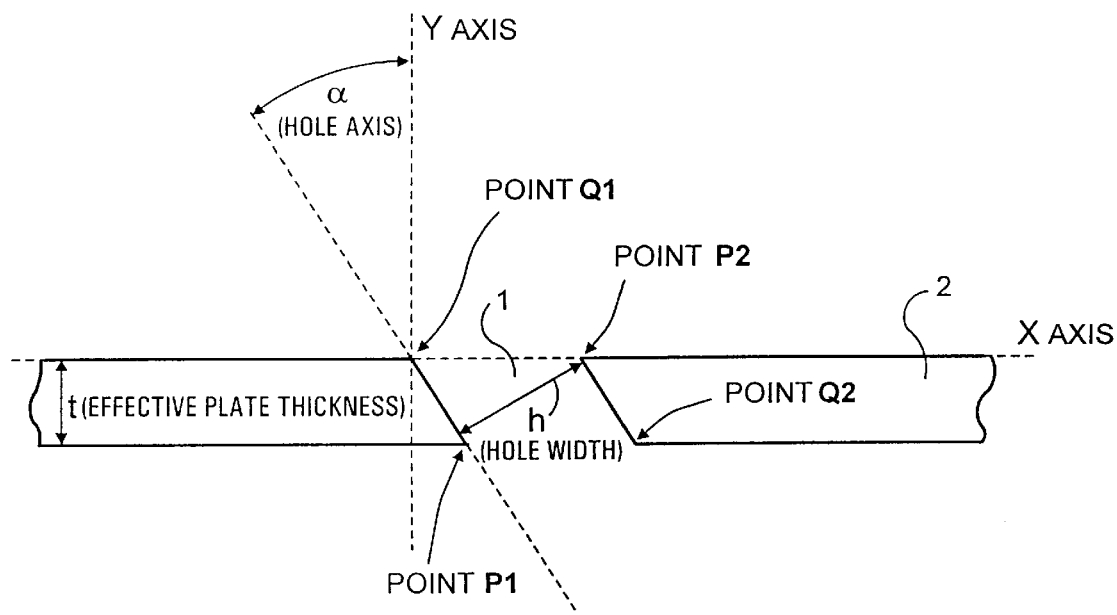
F I G. 3
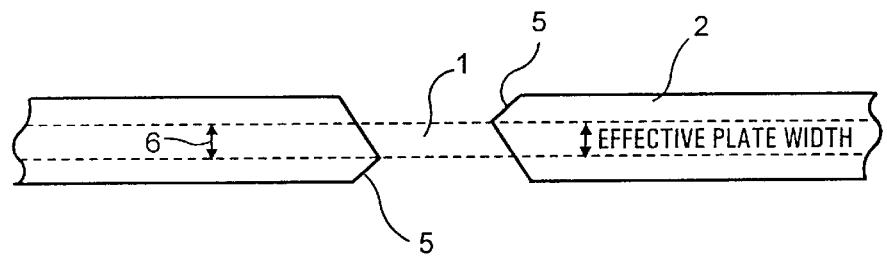
F I G. 4
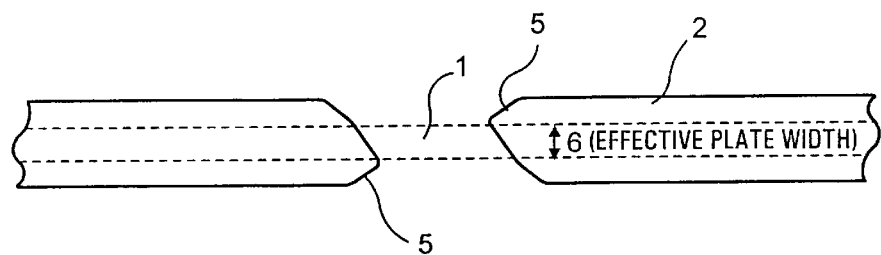
F I G. 5

METHOD OF ENABLING BONE SCREWS TO BE INSTALLED AT AN ANGLE IN UNDERLYING BONE

FIELD OF THE INVENTION

The invention relates to the installation of a bone fastener, such as a pin or screw, at an angle in a bone and particularly to the configuration of a support plate with a hole therein, such that the fastener can be inserted in the hole within a determined asymmetric angular range relative to a line perpendicular to the plate.

More specifically, the invention relates to a method of providing parameters for said plate and said hole to achieve said determined angular range.

BACKGROUND

Fractures of the bones in the human body are often fixed with implants that include plates and bone fasteners, such as pins and screws. The holes in these plates are oriented along an axis that is perpendicular to the surface of the plate, since this avoids "walking" of the drill as the hole is drilled in the plate and results in a cleaner hole. Furthermore, since the majority of screws are commonly inserted in an orientation that is perpendicular to the surface of the plate, this perpendicular orientation of the hole in most cases is the optimal design.

Occasionally, because of the local configuration of the fracture, it may be required to insert a screw at an angle that is not perpendicular to the surface of the plate, namely, an acute angle less than 90°. Since the typical screw hole is, in general, slightly oversized, the surgeon is able to angle the screw during insertion between opposite sides of the hole. Because the holes are placed perpendicular to the plate, the possible range of insertion angles is symmetrical from side to side. However, since most screws are placed in the shaft, or central region, of bone, this ability to angle the screw in opposite directions is often a useful feature.

There are some situations, however, during the fixation of fractures in which the local anatomy and/or geometry will only permit safe insertion of a screw within a predetermined limited range of screw insertion angles which is not symmetrical relative to an axis perpendicular to the plate surface. For instance, such a situation can occur during the application of a plate to the distal end of the radius, where certain directions of screw insertion to one side would result in penetration of the screw across the joint and into the articular surface, resulting in severe, progressive posttraumatic arthritis. Currently, there are no designs available that limit the possible range of insertion angles to a predefined range of values that is not symmetrical with respect to an axis perpendicular to the surface of the plate.

If a larger hole is provided in the plate to accommodate large oblique angles of insertion of the screw, this is not optimal for two reasons. First, this would allow the oblique angle of insertion to occur to either side of the plate which may not be desirable, such as in the case referred to above. Secondly, simply increasing the hole size in the plate results in the unwanted side effect of excessive lateral translation (or slop) of the screw in the screw hole. Rather, the optimal design should not only permit a predefined asymmetric range of insertion angles, but additionally provide a hole in the plate that is as small as possible, in order to limit translational movement of the screw in the plate.

The preceding discussion is equally applicable to the use of pins instead of screws through the plate hole.

SUMMARY OF THE INVENTION

An object of the invention is to provide a method by which the hole can be formed in the plate to provide a predetermined angular range for insertion of the fastener within asymmetric angular limits relative to a line perpendicular to the plate.

A further object of the invention is to provide the hole with a diameter which is the minimum to accommodate said predetermined angular range.

In order to achieve the above and other objects, the invention provides a method for determining parameters for an angulated hole in the plate so that a fracture fixation fastener can be installed at an acute angle in the underlying bone within a pre-determined angular range which is asymmetrical relative to a line perpendicular to said plate. This method of the invention comprises forming said plate with a determined thickness, forming said hole in the plate with a determined diameter and at a determined angle in said plate, and correlating said diameter and said angle of said hole relative to the thickness of the plate so that said fastener can be inserted in said hole within said pre-determined angular range and whose angular limits are asymmetrical relative to a line perpendicular to said plate.

BRIEF DESCRIPTION OF THE FIGURES OF THE DRAWING

FIG. 3 is a diagrammatic illustration for determining parameters of plate thickness and hole diameter.

FIG. 4 is a diagrammatic illustration showing a variation in the hole in the plate.

FIG. 5 is a diagrammatic illustration showing another variation in the hole in the plate.

DETAILED DESCRIPTION

The present invention provides a design for a hole 1 in a fixation plate 2 that allows a predetermined range of asymmetric angles of insertion $\theta_1$ to $\theta_2$ of a fixation or bone fastener 3, such as a screw or pin. The angles $\theta_1$ and $\theta_2$ are determined by the anatomy at the site of application and the location of the fasteners. This invention is applicable to situations in which $\theta_1 \neq \theta_2$. In addition, maximal constraint to translational movement of the pin or screw is achieved.

The invention is based upon a method of determining a particular relation between effective thickness (t) of plate 2, the diameter (d) of fastener 3, the diameter of the hole and the angle αx of the hole to obtain the desired range of insertion angles ($\theta_1$ to $\theta_2$).

Specifically, the hole I is drilled in the plate 2 with hole diameter h at angle α in accordance with the following relationship, wherein:

$$\alpha = \arctan(X_2 - X_1)/2t$$

$$h = (X_2/2 + X_1/2)(\cos \alpha)$$

where
 t=plate thickness and the variables $X_1$, $X_2$ are defined according to the relationship:

$$X_2 = d/\cos(\theta_2) + t(\tan(\theta_2))$$

$$X_1 = d/\cos(\theta_1) - t(\tan(\theta_1))$$

where $\theta_1$ = limit of insertion angle desired in one direction $\theta_2$ = limit of insertion angle desired in opposite direction, and d = maximal diameter of the fastener.

all angles being measured with reference to a line that is perpendicular to the surface of the plate.

The derivation of the above relationships will be explained with reference to FIGS. 1—3.

Figure 1:
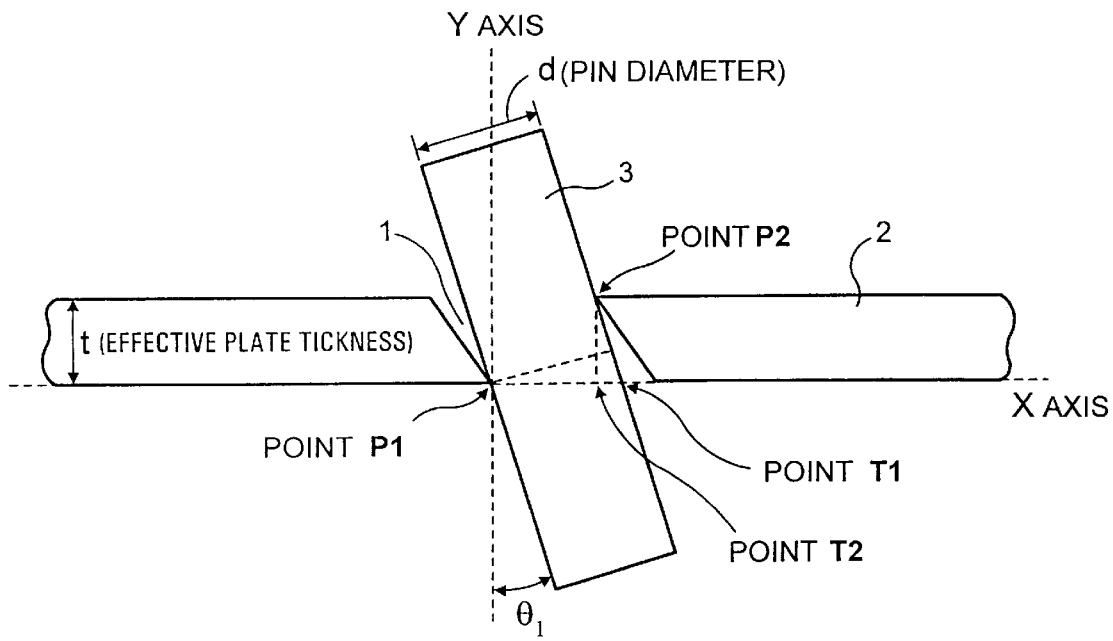
FIG. 1 is a diagrammatic illustration of a bone fastener in a hole in a plate in which the fastener is angulated to one side in a limit position.

Referring to FIG. 1, therein is seen an angulation of fastener 2 in hole 1 at a maximum clockwise angle of $\theta_1$ relative to an axis Y perpendicular to the plate. The right side of the fastener 2 in FIG. 1 contacts the hole at the upper surface of the plate at a point $P_2$ and the left side of the fastener in FIG. 1 contacts the hole at the lower surface of the plate at a point $P_1$. Point $T_1$ represents a point on the right side of the fastener in the plane of the lower surface of the plate. Point $T_2$ is a point of intersection between a line from point $P_2$ perpendicular to the plane of the lower surface of the plate 3.

From FIG. 1 it is seen that the distance between points $P_1$ and $T_1$ $(P_1{:}T_1)_x = d/\cos(\theta_1)$ the distance between points $T_2$ and $T_1$ $(T_2{:}T_1)_x = t(\tan \theta_1)$ The distance between points $P_2$ and $P_1$ measured in the X direction $(P_2{:}P_1)_x = d/\cos \theta_1 - t(\tan \theta_1)$, and the distance between points $P_2$ and $P_1$ measured in the Y direction $(P_2{:}P_1)_y = t$.

Figure 2:
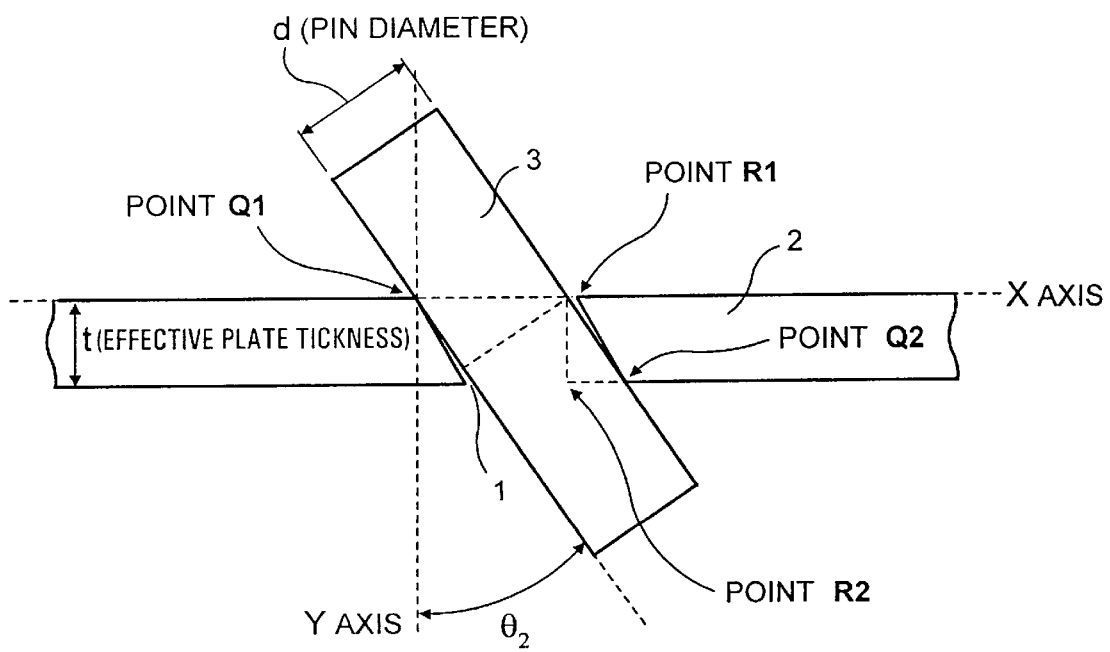
FIG. 2 shows the fastener of FIG. 1 in an angulated position in the hole in the plate to a limit position at the opposite side.

FIG. 2 shows the fastener 2 at a maximum counter-clockwise angulated position in hole 1 in which the fastener is at an angle $\theta_2$ relative to the Y axis. Point $Q_1$ represents a point on the left side of the fastener which contacts the hole at the upper surface of the plate 3 and point $Q_2$ represents the point of contact of the right side of the fastener with the hole at the lower surface of the plate 3. Point $R_1$ represents a point on the right side of the fastener located in the plane of the upper surface of the plate.

From FIG. 2 it is seen that the distance between points $Q_1$ and $R_1$ measured in the X direction $(Q_1{:}R_1)_x = d/\cos \theta_2$ the distance between points $R_2$ and $Q_2$ in the X direction $(R_2{:}Q_2)_x = t(\tan \theta_2)$ the distance between points $Q_2$ and $Q_1$ measured in the Y direction $(Q_2{:}Q_1)_y = t$, and the distance between points $Q_2$ and $Q_1$ measured in the X direction $(Q_2{:}Q_1)_x = d/\cos \theta_2 + t(\tan \theta_2)$ Reference is next made to FIG. 3 to obtain a relation between the diameter h of the hole, the thickness t of the plate and the angles $\theta_1$ and $\theta_2$ In FIG. 3 the distance between points $P_1$ and $Q_1$ measured in the X direction $= [(Q_1{:}Q_2)_x - (P_2{:}P_1)_x]/2$ wherein $(Q_1{:}Q_2)_x$ is the distance between points $Q_1$ and $Q_2$ measured in the X direction and $(P_1{:}P_2)_x$ is the distance between points $P_1$ and $P_2$ measured in the X direction.

$$\text{angle } \alpha = \text{arc tan } [(P_1{:}Q_1)_x/2]$$

wherein $(P_1{:}Q_1)_x$ is the distance between points $P_1$ and $Q_1$ measured in the X direction, and the diameter h of hole $1 = (P_2{:}Q_1)_x \cos \alpha$ where $P_2Q_1$ is the distance between points $Q_1$ and $P_2$ measured in the X-direction.

By introducing the relationships established with reference to FIGS. 1 and 2 into the expressions established in FIG. 3, it follows that $$\alpha = \text{arc tan}(X_2 - X_1)/2t$$

where $X_2 = d/\cos \theta_2 + t(\tan \theta_2)$, and $X_1 = d/\cos \theta_1 - t(\tan \theta_1)$, and Hole diameter $h = (X_2/2 + X_1/2) \cos \alpha$ In the above expressions, $\theta_1$ is the limit angle of insertion of the fastener in the hole in one direction.

$\theta_2$ is the limit angle of insertion of the fastner in the hole in the other direction, and wherein $\theta_1 \neq \theta_2$ t is the thickness of the plate, and d is the maximum diameter of the fastener.

In sum, the invention provides a method for establishing parameters for the diameter and angle of the hole in the plate, said angle being an acute angle other than 90°, and based upon the desired effective plate thickness, fastener diameter, and desired angles $\theta_1$ and $\theta_2$ for limiting the angle of insertion of the fastener in the hole relative to a line perpendicular to the surface of the plate. Thereby, fasteners can be fixed at an angle into the underlying bone within a predetermined asymmetric angular range.

In the illustrated embodiment, the plate is flat and the perpendicular is perpendicular to the plane of the plate. If the plate is curved, the perpendicular will be perpendicular to the surface of the plate, i.e. to the tangent at the surface of the plate.

FIG. 4 shows a variation in the hole in the plate in which a counter sink or bevel 5 is formed at the upper and lower surfaces of the plate. The effective plate thickness is shown by numeral 6. The relationships established in respect of FIG. 3 apply to the plate of FIG. 4 where the effective plate thickness 6 is used as the value of plate thickness t in the various expressions.

FIG. 5 is similar to FIG. 4 but shows the edge of the hole with a curved contour. Here also the effective width of the plate is shown and its value is used in the above expressions for thickness t.

In order to produce the holes in the plate without "walking" of the drill, the holes can be produced by a laser beam.

It can be seen that a hole of size h and directed at angle $\alpha$ will not only allow an asymmetric variation of insertion angle of the fastener between the range $\theta_1$ to $\theta_2$ along the axis of the hole, but additionally allow some symmetric variation of the insertion angle of the fastener from side to side in a plane that is perpendicular to the axis of the hole, as the hole is slightly oversized in relation to the maximal diameter of the fastener. It will be noted that further reduction in the side to side translational movement of the fastener within the hole may be achieved by narrowing the hole along this side to side axis, without affecting the asymmetric range of allowed insertion angles along the principal axis.

Furthermore, in order to provide separate asymmetric variation of the insertion angle of the fastener both along the axis of the plate as well as perpendicular to the axis of the plate, a hole can be formed along an axis that is oriented obliquely to the long axis of the plate.

Although the invention is disclosed with reference to particular embodiments thereof, it will become apparent to those skilled in the art that numerous modifications and variations can be made which will fall within the scope and spirit of the invention as defined by the attached claims.

What is claimed:

1. In a method of installing a fracture fixation fastener at an acute angle in an underlying bone by engaging the fastener in a hole in a support plate, the improvement by which the fastener can be engaged and supported in the hole in the plate within a pre-determined angular range which is asymmetrical relative to a line perpendicular to said plate, said improvement comprising:

forming said plate with a determined thickness, forming said hole in the plate with a determined diameter and at a determined angle in said plate, and correlating said diameter and angle of said hole relative to the thickness of the plate so that said fastener will be inserted into said hole within said pre-determined angular range and wherein said angular range provides desired asymmetric limit angles of insertion of said fastener relative to the line perpendicular to said plate.

2. The improvement as claimed in claim 1, wherein for a fastener having diameter d to be inserted within an angular range of insertion $\theta_1$ in a clockwise direction relative to a line perpendicular to the surface of the plate and within an angular range of insertion $\theta_2$ in a counterclockwise direction relative to a line perpendicular to the surface of the plate, wherein $\theta_1$ and $\theta_2$ are unequal, said hole is provided at angle $\alpha$ relative to a line perpendicular to the surface of the plate and with a diameter h, where $$\alpha = \text{arc } \tan(X_2 - X_1)/2t$$

$$h = (X_2 + X_1)(\cos \alpha)/2$$

where $\theta_1$ = limit of insertion angle desired in the clockwise direction $\theta_2$ = limit of insertion angle desired in the counterclockwise direction t = plate thickness d = maximal diameter of the fastener and the variables $X_1$, $X_2$ are defined according to the relationship:

$$X_2 = d/\cos(\theta_2) + t(\tan(\theta_2))$$

$$X_1 = d/\cos(\theta_1) - t(\tan(\theta_1))$$

all angles being measured from said line perpendicular to said plate.

3. The improvement as claimed in claim 2, wherein said hole is formed with countersinking at upper and lower surfaces to a particular depth in said plate, said value of thickness used in the above relationships being an effective thickness of the plate which is equal to the total thickness of the plate minus a sum of the countersinking depths at the upper and lower surfaces of the plate.

4. The improvement as claimed in claim 1, wherein the hole is formed by laser drilling.

* * * * *